United States Patent [19]

Harris

[11] 3,959,128

[45] May 25, 1976

[54] PROCESS FOR REMOVING ENDOTOXIN FROM BIOLOGICAL FLUIDS

[75] Inventor: Nick S. Harris, Galveston, Tex.

[73] Assignee: Preventive Systems, Inc

[22] Filed: Dec. 27, 1974

[21] Appl. No.: 536,833

[52] U.S. Cl. .............................. 210/24; 128/214 R; 128/DIG. 3; 210/DIG. 23; 424/78; 424/83; 424/101

[51] Int. Cl.² .......................................... B01D 15/00

[58] Field of Search ....... 128/214 R, 214 B, DIG. 3; 210/24, DIG. 23; 424/101, 78, 83

[56] References Cited

UNITED STATES PATENTS

| | | | |
|---|---|---|---|
| 3,770,631 | 11/1973 | Fekete et al. | 424/101 |
| 3,794,584 | 2/1974 | Kunin | 210/24 |

OTHER PUBLICATIONS

Hasselberger et al., "The Preparation of Insoluble, Matrix-supported Derivatives of Asparaginase for Use in Cancer Therapy", Cancer Research, Vol. 30, Nov. 1970, pp. 2736–2738.

Nolan et al., "Effect of Cholestyramine on Endotoxin Toxicity and Absorption", Digestive Diseases, Vol. 17, No. 2, Feb. 1972, pp. 161–166.

*Primary Examiner*—Charles N. Hart
*Assistant Examiner*—Ivars Cintins
*Attorney, Agent, or Firm*—Pravel & Wilson

[57] ABSTRACT

A novel process for removing endotoxin from biological fluids such as parenteral fluids and for removing or reducing the level of endotoxin from the blood of animals is disclosed. The novel process includes the utilization of certain non-ionogenic hydrophobic synthetic plastic polymers that have been found to be capable of adsorbing endotoxin from the biological fluids when placed in intimate contact therewith.

15 Claims, No Drawings

PROCESS FOR REMOVING ENDOTOXIN FROM BIOLOGICAL FLUIDS

BACKGROUND OF THE INVENTION

This invention relates to the removal of endotoxin from biological fluids including the blood of animals and parenteral fluids such as serum, plasma, whole blood, albumins, dextrose solutions, and the like. More particularly, the invention pertains to a novel process for removing endotoxin from such biological fluids through the use of certain nonionogenic hydrophobic snythetic plastic polymers or resins that are capable of adsorbing endotoxin present in the fluids.

Generally speaking, endotoxin is a complex lipopolysaccharide material derived from gram-negative bacilli that is known to produce a wide variety of striking pathophysiological reactions in animals. Studies have demonstrated that endotoxin is distinguishable from classic protein toxins due to its failure to be neutralized by anti-serum, its increased heat stability and its failure to be converted to toxoid by treatment with formaldehyde. Moreover, endotoxin exhibits a lesser degree of potency than classic protein toxins and produces essentially similar reactions in animals regardless of the microbial origin of the endotoxin. The material has been known and studied for many years particularly in regard to the pathophysiological reactions it causes in animals. For many years it was believed that the material was contained within gram-negative bacilli cells and was released only upon disintegration of the cell walls. Hence, the material was termed endotoxin. Recent studies, however, have shown that endotoxin is localized at the cell surface of gram-negative bacilli and may be present with viable and killed cells as well as in a free form within a liquid medium.

As mentioned before, endotoxin is known to cause several striking and varied pathophysiological reactions and has been identified as a direct and contributory cause of death of many hospitalized patients. More particularly, exdotoxin is known to cause febrile reactions in animals with symptons of extremely high fever, vasodilation, diarrhea, and the like and, in extreme cases, fatal shock. It is also known the endotoxin causes leucocytosis, deleterious changes in carbohydrate and protein metabolism and widespread intravascular clotting by fibrin formation.

Studies have shown that endotoxemia in animals may be caused by or is associated with gram-negative bacilli primary and secondary infections and/or the employment of intravenous apparatus or solutions contaminated with gram-negative bacilli or endotoxin. The occurrence of endotoxemia from the use of endotoxin-contaminated intravenous or parenteral solutions has recently been recognized as a particular problem in modern hospitals. In addition, it has recently been found that severe trauma, particularly trauma caused by thermal injuries, may cause the release of endotoxin from gram-negative bacilli of the normal flora of the gastrointestinal tract of animals. The studies have shown that there may be increased levels of endotoxin in the blood of traumatized animals even when the animals have no other diagnosed bacterial infection.

Under normal conditions the blood cells, i.e., leucocytes, of animals usually control the level of endotoxin in the blood. However, the blood cells usually cannot control excessive amounts of endotoxin experienced under abnormal conditions, such as those hereinabove mentioned, thereby resulting in endotoxemia. It is presently a common practice in the medical profession to counteract endotoxemia by treatment with massive infusions of antibiotics. However, it has not been shown that antibiotics remove endotoxin other than by controlling gram-negative bacilli. As mentioned hereinbefore, endotoxin is known to exist in free form in liquid media and may be associated with killed bacterial cells.

There are a few procedures known for removing or reducing the level of endotoxin in certain fluid media. For example, endotoxin may be removed from a liquid medium by filtration procedures employing macromolecular and/or activated carbon filters whereby the complex endotoxin molecules are filtered out. Osmotic pressure separation procedures have also been employed. These techniques have generally been employed in the purification of water and relatively simple fluid compositions. However, such techniques have not been extensively used to remove endotoxin from biological fluids. particularly certain parenteral fluids such as plasma, serum, albumins, whole blood and the like, apparently due to the extremely complex molecular and sometimes cellular composition of such fluids. In fact, it is common practice in the medical and pharmacological professions to merely destroy parenteral fluids contaminated with unacceptable levels of endotoxin.

I have now discovered a process for selectively removing endotoxin from substantially any biological fluid which does not otherwise adversely affect the molecular and/or cellular composition of the fluid. In fact, the process of my invention is particularly useful in removing and/or reducing the level of endotoxin in the blood of animals in accordance with in vivo hemoperfusion techniques. The inventive process is based upon the surprising discovery that certain non-ionogenic hydrophobic synthetic plastic polymers have specific affinity for endotoxin when placed in intimate contact therewith.

Several types of synthetic plastic resins or polymers have heretofore been used in various processes for treating parenteral fluids and/or blood. For example, there are several known procedures for treating parenteral fluids by the employment of ion exchange resins. More particularly, ion exchange resins have been employed in processes for treating parenteral fluids, including blood, with anionic and cationic agents, for separating certain protenatious materials from blood, for preparing sterile parenteral fluids difficult to sterilize such as bicarbonate ion solutions, and the like. See U.S. Pat. Nos. 3,769,401; 3,097,141; 3,234,199; 2,682,268; and 3,305,446 to name a few. The ion exchange resins employed in these processes are basically comprised of monomers and/or polymers of styrene or vinyl benzene treated with many types of polyelectrolytes.

U.S. Pat. No. 3,794,584 teaches a process for removing poisonous or toxic amounts of barbiturates and glutethimides from blood which includes perfusing blood over a column of an essentially non-ionogenic macroreticular watersoluble cross-linked polymer having a porosity of at least 10% and a specific surface area of at least 10 square meters per gram. The polymer resin employed is described as being comprised of from 2 to 100 weight percent of a poly(vinyl)-benzene monomer polymerized with 1 or more mono- or polyethylenically unsaturated monomers. The disclosed poly-(vinyl)benzene-based macroreticular polymer resins are described as being capable of adsorbing the barbiturates and glutethimides from the blood without otherwise adversely affecting the blood.

U.S. Pat. No. 3,706,661 teaches a method for the separation of biological cells from solutes by the use of macroporous synthetic plastic resin gels, particularly gels of polyacrylamide and hydrophilic polymethacrylates. U.S. Pat. No. 3,839,314 describes a process of clarifying blood serum and plasma to remove undesired protenatious and lipid matter by the employment of block copolymers of ethylene oxide and a polyoxypropylene polymer. There are also several prior art references which describe the use of certain synthetic plastic resins, such as nylon, acrylonitrile polymers, polyesters, and polytetrafluoroethylene in fiber or textile form as filter media to remove materials from certain parenteral fluids. See U.S. Pat. Nos. 3,462,361; 3,448,041; 3,035,575, 3,533,400; and 2,702,036.

However, to my knowledge, the synthetic polymeric resins that I have found to be capable of adsorbing endotoxin have not heretofore been specifically employed in any prior art processes for treating biological fluids, particularly for removing endotoxin. Furthermore, many types of synthetic resins heretofore employed in processes for treating biological fluids to remove certain components have been found to have no affinity for endotoxin.

SUMMARY OF THE INVENTION

The present invention is a novel process for removing endotoxin from biological fluids such as parenteral fluids and for removing ore reducing the level of endotoxin from the blood of animals which comprises intimately contacting a biological fluid contaminated with endotoxin with a nonionogenic hydrophobic non-polar aliphatic synthetic polymer or resin capable of adsorbing endotoxin which may be selected from the group consisting of substantially crystalline non-polar aliphatic hydrocarbon thermoplastic polymers, fluorocarbon polymers, silicone elastomeric polymers, and mixtures thereof. The biological fluid may then be removed from intimate contact with the polymer or resin essentially free of endotoxin. The endotoxin remains tightly bound to the polymer material. The invention represents a tremendous advance in the art for it provides a process for directly and selectively removing endotoxin from substantially any type of biological fluid, even those of highly complex composition. Moreover, the process of the invention can be employed in an in vivo hemoperfusion process ro remove and/or reduce the level of endotoxin in the blood of animals.

DETAILED DESCRIPTION OF THE INVENTION

In accordance with the present invention, synthetic plastic polymers or resins that have been found to be capable of adsorbing endotoxin are normally hydrophobic, non-ionogenic and substantially non-polar. These polymers are also aliphatic saturated materials. More particularly, types of synthetic plastic polymers that have been found capable of adsorbing endotoxin include substantially crystalline, non-polar aliphatic hydrocarbon thermoplastic polymers, fluorocarbon polymers, silicone elastomers and mixtures thereof. The mechanism whereby these types of synthetic plastic polymers adsorb endotoxin is not understood. Experiments have shown that when a biological fluid contaminated with endotoxin is contacted with these types of polymers the endotoxin is readily removed from the liquid media. These experiments have further shown that the endotoxin removed is tightly bound to the synthetic polymer surface and is not readily removed by simple washing. Yet, many types of synthetic polymer or resin materials heretofore employed for removing certain types of components from biological fluids have been found to be incapable of adsorbing endotoxin. Examples of some of these materials include polystyrene, nylon (polyamide), poly(methylmethacrylate), and polycarbonate, to name a few.

These synthetic polymer materials that have been found to be incapable of adsorbing endotoxin are, generally, amorphous, atactic polymers. Many of these polymers also contain aromatic groups and/or are ethylenically unsaturated. Conversely, as mentioned hereinbefore, the types of polymers that have been discovered to have an affinity for and are capable of adsorbing endotoxin are generally aliphatic saturated polymers which are non-ionogenic, substantially non-polar and hydrophobic. Moreover, many of these polymers are classified as crystalline, isotactic polymers.

The substantially crystalline non-polar aliphatic hydrocarbon thermoplastic polymers preferably employed in the process of the invention include the poly-$\alpha$-olefins, such as polyethylene, polypropylene, and the higher homologue polymers. Any commercially available type or grade of poly-$\alpha$-olefin may be employed in substantially any molecular weight commercial formulation. The polymers may include inert compatible fillers and/or colorant with no adverse affect on their capability of adsorbing endotoxin. Moreover, copolymers may be employed. Examples of particular commercially available poly-$\alpha$-olefins that have been found useful include high density polyethylene, low density polyethylene, and isotactic polypropylene, to name a few.

Fluorocarbon polymers have also been found to have an affinity for endotoxin and are extremely useful in the process of the invention. As known, fluorocarbon polymers are highly crystalline, hydrophobic, non-ionogenic and substantially non-polar thermoplastics. Any commercially available fluorocarbon polymer material may be employed in the inventive process, including those substituted with other halogens, such as chlorine, and those formulated with inert filler or colorant ingredients. Types of fluorocarbon polymers that have been found to the particularly useful include tetrafluoroethylene polymers, fluorinated ethylene-propylene polymers and modified copolymers of tetrafluoroethylene and ethylene. These polymers are readily available commercially in a variety of grades. For example, fluorinated ethylene-propylene polymers are sold by E. I. du Pont de Nemours & Co., Inc. under the trademark TEFLON FEP. Modified copolymers of tetrafluoroethylene and ethylene are also sold by E. I. du Pont de Nemours & Co., Inc. under the trademark TEFZEL.

Furthermore, any type of silicone elastomer may be employed in the process of the invention. Silicone elastomers are classified as thermosetting cross-linked synthetic polymers and are normally quite resilient. Thus, their physical characteristics are somewhat different from the crystalline non-polar aliphatic hydrocarbon polymers and fluorocarbon polymers mentioned hereinabove. Yet, experiments have shown that silicone elastomers have an affinity for endotoxin and are capable of adsorbing it from a liquid medium. Types of silicone elastomers that are particularly useful in the process of the invention include the high molecular weight linear poly(alkylsiloxane)s that are cured by cross-linking linear or slightly branched siloxane chains having reactive silanol end groups. These silicone elastomers are generally referred to in the art as room-temperature vulcanizing silicone elastomers and are readily available commercially. Any of these commercially available materials may be employed, including those containing inert filler and/or colorant ingredients. Examples of suitable silicone elastomers include the RTV 732 and 108 silicone elastomers sold by Dow Corning Company, which contain dimethyldichlorosilane and cross-linking agents that cure by cross-linking when exposed to atmospheric moisture. Another suitable silicone elastomer is medical grade silastic sold by Dow Corning Company which is cross-linked and cured at room-temperature by the addition of stannous octoate. These silicone elastomers are employed in the process of the invention after they have been cured or cross-linked to form solidified materials which are then particulated.

In carrying out the process of the invention the non-ionogenic hydrophobic synthetic polymer or resin is preferably utilized in particulate form such as granules, beads, irregular chips, fibrous strands and the like to provide increased surface area per volume or weight. The particulate size and volume of polymer employed has not been found to be particularly critical. However, it is preferred to employ substantially spherical beads or granules of the polymer when highly complex fluids containing biological cells are treated so as to prevent damage and/or agglomeration of the cells, particularly blood cells. Moreover, it is preferred to employ the particulated synthetic polymer or resin in a volume excess of that required to remove substantially all endotoxin from a contaminated biological fluid. The volume of polymer or resin employed is variable, depending upon the degree of endotoxin contamination, polymer particulate size, and volume of fluid to be treated. The particular volume of polymer or resin employed for treating a given sample of a biological fluid is best determined emperically and may be readily determined by one having ordinary skill in the art without undue experimentation. It is particularly preferred to employ losely packed columns of polymer beads or granules having a diameter of about 0.5 mm to about 4 mm.

Further, in carrying out the process of the invention the biological fluid contaminated with endotoxin is preferably passed or perfused through the column containing the above-described particulated synthetic polymer or resin at a volume flow rate sufficient to provide an intimate contact of the endotoxin with the polymer surface. A gravitational flow rate has been found to be usually sufficient. In addition, it is preferred to slightly agitate the column of particulated polymer material as the biological fluid is passed over so as to enhance contact of the endotoxin with the polymer surface. Slight agitation is particularly helpful when the biological fluid being treated contains biological cells, such as whole blood, to reduce agglomeration of the cells.

As mentioned hereinbefore, the process of the invention may be employed to effectively remove endotoxin from substantially any type of biological fluid including parenteral fluids and may also be employed in an in vivo hemoperfusion technique to remove and/or reduce the level of endotoxin in the blood of animals. Examples of parenteral fluids that may be treated by the process include saline solutions, dextrose solutions, hyperalimentation fluids, serums, plasma, albumins, whole blood, and antiserums, to name a few. When treating such parenteral fluids by the process of the invention, it is preferred to pass the parenteral fluid by gravitational flow over a column containing the above described particulated synthetic polymer or resin. Preferably, the parenteral fluid is treated immediately before use so as to reduce the possibility of later contamination. The parenteral fluid passed through the polymer column may then be directly injected into the patient essentially free of endotoxin contamination.

In a preferred embodiment the process of the invention may be employed for removing and/or reducing the level of endotoxin in the blood of an animal by an in vivo hemoperfusion polymer-column technique. More particularly, in this preferred embodiment, heparinized blood from an animal is removed through an arterial bypass and perfused through a column containing granules or beads of one or more of the above-described synthetic polymers capable of removing endotoxin. Preferably about 50 to about 250 grams of the polymer beads or granules, having an average particle size of from about 0.5 mm to about 4.0 mm diameter, are employed per kilogram weight of the animal. The perfused blood from the polymer-column is then reinfused into the animal. Preferably, during perfusion the polymer-column is slightly agitated to reduce the possibility of agglomeration of blood cells. The process may be continued as long as desirable and has been found to effectively remove and control the level of endotoxin in the blood of the animal as shown by some of the examples set forth hereafter. Moreover, the process has not been found to adversely affect the blood cells in the blood of the animal.

The following examples particularly illustrate the nature of the inventive process but are not intended to be limitative thereof. In the following examples the presence and amount of endotoxin present were determined by the use of the Limulus Lysate Assay, which is an assay based on the gelation of amebocyte lysate from *Limulus polyphemus*, the horseshoe crab. The Limulus Lysate Assay has been described as the most sensitive method presently available for the detection of endotoxin. See R. R. Rojas-Corona, et al. "The Limulus Coagulation Test for Endotoxin: A Comparison With Other Assay Methods", Proceedings of the Society for Experimental Biology and Medicine 132, 599–601 (1969); and James H. Jorgensen et al. "Measurement Of Bound And Free Endotoxin By The Limulus Assay", Proceedings of the Society for Experimental Biology and Medicine 146, 1024–1031 (1974). The assay is performed by incubating a sample of a fluid suspected of containing endotoxin with an equal volume of the amebocyte lysate from the horseshoe crab, *Limulus polyphemus*. The degree and quality of gelation observed is directly related to the amount of endotoxin present. The assay has been found to be so sensitive so as to detect as little as 0.1 nanogram of endotoxin.

The Limulus lysate employed in the following examples for the respective assays was prepared in accordance with a known published procedure for lysing amebocytes of the hemolymph of Limulus crabs. The crabs were obtained from the Marine Biological Laboratory, Woods Hole, Mass. The amebocyte cells were lysed by the addition of pyrogen-free distilled water at a 1:3 ratio of packed cells to water. The suspension was then thoroughly mixed and allowed to stand at 4°C. for 18–24 hours. The cellular debris was then removed by centrifugation and the lysate decanted. The lysate was stored in sterile pyrogen-free polystyrene vials at −20°C., or for shorter periods of time at 4°C., until needed.

EXAMPLE I

An endotoxin standard was prepared by adding 10 mg endotoxin to 10 ml pyrogen-free saline (0.9% sodium chloride) to yield a solution of 1 mg/ml concentration. The endotoxin used was a lipopolysaccharide Westphal phenol extract of *Escherichia coli* 011:B4, sold by Difco Laboratories, Detroit, Michigan. This initial 1 mg/ml endotoxin concentration solution was then diluted several times with pyrogen-free saline using dilution factors of 1:10 to provide several samples having endotoxin concentrations of 100 ng/ml, 10 ng/ml and 1 ng/ml. A sample having an endotoxin concentration of 0.5 ng/ml was also prepared. These endotoxin standard solutions were prepared in polystyrene test tubes sold by Falcon Plastics, Oxnard, California. A 1.0 ml sample of the endotoxin solution having a concentration of 100 ng/ml was then added to a polystyrene test tube (Falcon Plastics, supra) containing 2 cc of raw polypropylene beads, about 2 mm average diameter, (Shell Polypropylene 5520, Shell Chemical Company, Houston, Texas) and held for 10 minutes at room-temperature with gentle shaking every three minutes. 0.1 cc of this sample as well as 0.1 cc from several other samples of the endotoxin standard solution were then collected for assay. The assay was conducted by adding the 0.1 cc samples to 0.1 cc, respectively, of Limulus lysate. Each sample assayed was incubated with the lysate for 70 minutes at 37°C. The resultant reactions were observed and graded for degree and quality of gelation as follows:

+4 Firm clot and cloudy.
+3 Soft clot which slides down inverted tube, cloudy.
+2 High viscosity slime and cloudy.
+1 Medium viscosity and maybe cloudy.
0 Substantially clear, like water.

The results of the assay of the samples are set forth in the following Table 1.

TABLE 1

| Tube | Content | Concentration ng/ml | Reaction |
|---|---|---|---|
| 1 | Saline (control) | 0 | 0 |
| 2 | Endotoxin standard | 100 | +4 |
| 3 | Endotoxin standard | 10 | +4 |
| 4 | Endotoxin standard | 1 | +3 |
| 5 | Endotoxin standard | .5 | +2 |
| 6 | Treated Endotoxin standard | 100 | +2 |

As the results of Table 1 show, the polypropylene beads effectively removed over 99% of the endotoxin present in the treated sample, Tube 6. This 100 ng/ml endotoxin concentration sample should have given a +4 reaction, as Tube 2. However, surprisingly, it reacted substantially similar to the 0.5 ng/ml endotoxin standard sample analyzed.

EXAMPLE II

Two 12 cc syringes were respectively filled with 10 cc of two types of raw polypropylene beads (Shell Polypropylene 5520 and Shell Polypropylene 5820, Shell Chemical Company, supra). A third 12 cc syringe was filled with 10 cc of nylon fibers obtained from a Fenwal Leucopack filter (Baxter Laboratories, Inc., Chicago, Illinois). A fourth 12 cc syringe was filled with 10 cc of polystyrene chips prepared by particulating polystyrene test tubes (Falcon Plastics, supra) into approximately 8 mm × 2 mm × 6 mm chips. To each syringe was added 3.0 cc of the endotoxin standardized solution prepared in Example I at a concentration of 100 ng/ml endotoxin. The endotoxin standard solutions passed through the respective polymer columns by gravitational flow and were collected for assay. The treated solutions were then assayed utilizing the Limulus Lysate Assay as described in Example I along with several endotoxin standard solutions at various concentrations for comparison. The results of the assays are set forth in the following Table 2.

TABLE 2

| Sample No. | Material | Concentration[1] ng/ml | Reaction |
|---|---|---|---|
| 1 | Endotoxin Standard | 100 | +4 |
| 2 | Endotoxin Standard | 10 | +4 |
| 3 | Endotoxin Standard | 5 | +4 |
| 4 | Polypropylene[2] | 100 | +3 |
| 5 | Polypropylene[3] | 100 | +2 |
| 6 | Nylon | 100 | +4 |
| 7 | Polystyrene | 100 | +4 |

[1]Endotoxin concentration. Original concentration of solutions before treatment.
[2]Shell Polyproopylene 5520, Shell Chemical Company.
[3]Shell Polypropylene 5820, Shell Chemical Company.

A comparison of the assay reaction results of Table 2 illustrate that the treatment of the endotoxin solutions in accordance with the present invention utilizing polypropylene beads resulted in removal of endotoxin from the solutions to a level of below 5 ng/ml. The results of Table 2 also show that nylon and polystyrene were ineffective in removing the endotoxin from the test solutions.

EXAMPLE III

In this example several experiments were conducted to determine the capability of various types of synthetic polymers or resins for removing endotoxin from a saline solution, employing the procedures described in Example I. Several endotoxin standard solutions were freshly prepared by initially adding 10 mg endotoxin (Westphal phenol extract of *Escherichia coli* 011:B4, Difco Laboratories, supra) to 10 ml pyrogen-free saline (0.9% sodium chloride). The resulting solution of 1 mg/ml endotoxin concentration was then diluted several times with the pyrogen-free saline to get several samples having final concentrations of 100 ng/ml, 10 ng/ml, 5 ng/ml, 2.5 ng/ml and 1 ng/ml endotoxin. The endotoxin solutions were then mixed with Limulus lysate for standardization employing the Limulus Lysate Assay procedure described in Example I which resulted in the following reactions:

| Endotoxin Solution-Lysate Standardization | | |
|---|---|---|
| Endotoxin Concentration | | Limulus Lysate Assay Reaction |
| 0 | (saline control) | 0 |
| 100 | ng/ml | +4 |
| 10 | ng/ml | +4 |
| 5 | ng/ml | +4 |
| 2.5 | ng/ml | +3 |
| 1 | ng/ml | +1 to +2 |

1 ml aliquots of three standardized endotoxin solutions having concentrations of 100 ng/ml, 10 ng/ml and 1 ng/ml, respectively, were then added to various types of particulated synthetic polymer or resin materials in the form of beads or chips having average particle sizes of about 2 mm in 10 cc polystyrene tubes (Falcon Plastics, supra) and allowed to sit at room-temperature for 10 minutes. 0.1 ml of each solution sample was then removed and assayed using the Limulus Lysate Assay procedure described in Example I. The types of synthetic polymers and amounts tested and Limulus Lysate Assay reaction results of each solution at each concentration are set forth in the following Table 3.

TABLE 3

| Synthetic Polymer | Particle form | Weight, grams | Lysate Assay Reaction | | |
|---|---|---|---|---|---|
| | | | 100 ng/ml | 10 ng/ml | 1 ng/ml |
| Polypropylene | beads | 2.4 | +3 | +2 | +1 |
| Polyethylene[2] | beads | 5.9 | +2 | +1 | +1 |
| Spun glass | fibers | .5 | +4 | +4 | +1 |
| Poly(methyl-methacrylate | chips | 5.0 | +4 | +4 | +1 |
| Silicone Elastomer[3] | chips | 3.8 | +3 | +1 | +1 |
| Silicone elastomer[4] | chips | 3.7 | +4 | +2 | +1 |
| Silicone Elastomer[5] | chips | 3.9 | +1 | +1 | +1 |

[2] Alathon 7040 high density polyethylene, E. I. du Pont de Nemours & Co., Inc.
[3] RTV 732 dimethyldichlorosilane; Dow Corning Co. Elastomer was room-temperature vulcanized by exposure to atmosphere for 48 hours and cut into chips, about 2 mm diameter, prior to use.
[4] RTV 108 dimethyldichlorosilane; Dow Corning Co. Also room-temperature vulcanized and cut into chips prior to use as (3).
[5] SIL 382 medical grade silastic cross-linked and cured by addition of stannous octoate; Dow Corning Co. After 48 hours, cut into chips prior to use.

A comparison of the results of the above Table 3 with the endotoxin solution Lysate standardization of this Example demonstrates the ability of poly-α-olefins and silicone elastomers to adsorb endotoxin even when merely placed in intimate contact with the endotoxin contaminated solutions. Of the endotoxin standardized solutions employed in this Example, these materials effectively lowered the concentration of endotoxin to below about 2.5 ng/ml. The results of Table 3 also illustrate that spun glass fibers, and poly-(methylmethacrylate) chips, conventionally used parenteral fluid filter materials, do not readily adsorb or exhibit an affinity for endotoxin.

EXAMPLE IV

In this example five types of synthetic polymer materials were employed to determine their capability of adsorbing endotoxin when employed in accordance with the process of the invention. The synthetic polymers employed were: polypropylene beads (Shell Polypropylene 5820, supra; polyethylene beads (Alathon 7040 high density polyethylene, supra); TEFLON FEP 100 fluorinated ethylene-propylene polymer (E. I. du Pont de Nemours & Co., Inc.); TEFZEL 200 modified copolymer of ethylene and tetrafluoroethylene (E. I. du Pont de Nemours & Co., Inc.); and polypropylene staple fiber (Hercules, Inc.). All of these polymer materials were washed with pyrogen-free distilled water. The polymer beads had an average size of about 2 mm. The polypropylene staple was also washed in a 70% solution of ethanol, pryogen-free saline and then pryogen-free distilled water. Each of the polymer materials were then respectively placed in 12 cc syringes to the 12 cc level. 1 cc aliquots of the endotoxin solution prepared and standardized as described in Example III, having an endotoxin concentration of 50 ng/ml, were then perfused through the syringes by gravitational flow. 0.1 cc of each treated solution was then added to 0.1 cc of the Limulus lysate, incubated at 37°C. for 70 minutes and the resultant reaction was observed and graded for degree and quality of gelation. The results are set forth in the following Table 4.

TABLE 4

| Synthetic Polymer | Endotoxin Concentration ng/ml[1] | Lysate Assay Reaction |
|---|---|---|
| Endotoxin Control | 50 | +4 |
| Endotoxin Control | 10 | +4 |
| Endotoxin Control | 5 | +4 |
| Endotoxin Control | 2.5 | +3 |
| Endotoxin Control | 1 | +1 to +2 |
| Polypropylene | 50 | +3 |
| Polyethylene | 50 | +3 |
| TEFLON FEP 100 | 50 | +2 |
| TEFZEL 200 | 50 | +2 |
| Polypropylene staple | 50 | +3 |

[1] Endotoxin concentration prior to treatment.

The results of Table 4 illustrate the capability of fluorocarbon polymers for adsorbing endotoxin. The results of this table also demonstrate the affinity of polypropylene to endotoxin in various particulate forms and confirm the results obtained with regard to polypropylene and polyethylene in the previous examples.

EXAMPLE V 100 ng of endotoxin (lipopolysaccharide Westphal phenol extract, E. coli 011:B4, Difco, supra) was seeded in 1.0 ml normal human serum albumin, USP 25% salt poor, (sold under the tradename METALBUMEN by Metabolic, Inc., Houston, Texas) in a pyrogen-free polystyrene tube. A 1.0 ml sample of the albumin was also added to a second pyrogen-free polystyrene tube. Two polypropylene beads (Shell Polypropylene 5820, supra), having diameters of about 2 mm, were respectively placed in each of the tubes. The samples were incubated at 37°C. for 10 minutes. The two beads were then removed, washed with pyrogen-free saline, and assayed for the presence of endotoxin by adding each bead to 0.1 ml Limulus lysate, incubating at 37°C. for 70 minutes and grading the resultant reaction for degree and quality of gelation in accordance with the Limulus Lysate Assay procedure described in Example I. Several endotoxin solutions at various concentrations were prepared by dilution of the endotoxin in saline, as described in Example I. 0.1 ml of the prepared endotoxin solutions, along with a 0.1 ml sample of the albumin were also assayed by the Limulus Lysate Assay as controls. The results of the assays are set forth in the following Table 5.

TABLE 5

| Material Assayed | Endotoxin Concentration, ng/ml | Limulus Lysate Assay Reaction |
|---|---|---|
| Endotoxin Control | 100 | +4 |
| Endotoxin Control | 10 | +4 |
| Endotoxin Control | 1 | +2 |
| Albumin Control | — | +1 |
| Polypropylene bead[1] | 100 | +4 |
| Polypropylene bead[2] | — | 0 |

[1]Bead placed in 1 ml albumin seeded with 100 ng endotoxin, incubation at 37°C. for 10 minutes. Bead washed with saline prior to assay.
[2]Bead placed in 1 ml albumin control, incubation at 37°C. for 10 minutes. Bead washed with saline prior to assay.

The results of Table 5 illustrate the endotoxin present in albumin was adsorbed by polypropylene and the adsorbed endotoxin was tightly bound to the polypropylene bead surface. The polypropylene bead contacted with the endotoxin seeded albumin gave a strong +4 assay reaction even after being washed with pyrogen-free saline.

EXAMPLE VI

A hemoperfusion polymer-column apparatus was designed to perform an arterial-venous shunt or bypass to determine the effectiveness of the inventive process for removing and/or reducing the level of endotoxin in the blood of an animal in vivo. The hemoperfusion polymer-column unit was prepared by packing a sephadex gel reservoir, 5 mm diameter, 30 cm long, with 800 g. of polyethylene beads having diameters of about 2 mm, average, (ALATHON 7040 high density polyethylene, Du Pont, supra). Intravenous tubes were attached to each end of the reservoir and capped with cathethers. The apparatus was then attached to a dog, weighing 12 kilograms, by injecting one catheter into an artery and the other catheter into a vein. The dog had previously been heparinized by injection with sigma pyrogen-free heparin at a dose level of about 6 units per cc of blood (approximate dose, 6000 units heparin). The blood from the animal was removed through the arterial intravenous line, perfused through and over the polyethylene bead column and reinfused through the venous intravenous line. The column containing the polyethylene beads was gently shaken by the use of a reciprocal shaker to prevent agglomeration of blood cells. After 1 hour of continuous perfusion no hemolysis was observed. The dog was then intravenously injected with 5 mg/kg weight endotoxin (lipopolysaccharide Westphal phenol extract of E. coli, 055:B5, Difco Laboratories, supra; reconstituted with pyrogen-free saline, 0.9% sodium chloride). This level of endotoxin injection is generally referred to as a LD-80 dose, which is an amount sufficient to be fatal to 80% of dogs injected within a 6 hour period. After injection the dog's vital signs were continously monitored. During this time the dog developed hypotension, hypoxia, metabolic acidosis, hypocapnia, and tachypnia. The arterial-venous bypass through the hemoperfusion polymer-column apparatus was continued for 1.5 hours after the endotoxin injection and then the apparatus was removed. 3 hours after the endotoxin injection, the dog was observed as to be resting comfortably with normal signs. Observation was continued for 24 hours after which the mentioned symptoms of acute endotoxemia no longer appeared.

EXAMPLE VII

In this example, a hemoperfusion apparatus was prepared in accordance with the design described in Example VI, except that the ends of the sephadex gel reservoir were covered with cotton gauze to prevent clogging and 800 g. of polypropylene beads, having average sizes of about 2 mm, were placed in the reservoir (Shell Polypropylene 5820, supra). This hemoperfusion polymer-column apparatus was attached to a dog weighing 17 kg as described in Example VI. After about 1 hour of continuous bypass of the blood perfused through the polymer-column no hemolysis was observed. The dog was then injected with 5 mg/kg weight of the endotoxin and perfusion of the blood through the polymer-column was continued for 1½ hours thereafter. A few minutes after the endotoxin injection the animal developed the symptoms of acute endotoxemia described in Example VI. The arterial-venous shunt was then discontinued by removal of the hemoperfusion apparatus. The polypropylene beads in the reservoir were then washed by perfusing pyrogen-free saline through the polymer-column. One of the beads was removed and added to 0.1 cc saline. 0.1 cc of the Limulus lysate was then added thereto and incubated at 37°C. for 70 minutes. During the incubation, a clot appeared.

The results of Examples VI and VII demonstrate the effectiveness of the process of the invention for removing and/or reducing the level of endotoxin in the blood of animals when employed in an in vivo hemoperfusion or arterial-venous bypass technique whereby blood from the animal is removed, perfused through a column of the polymer capable of adsorbing endotoxin and then the blood is reinfused into the animal. Moreover, Example VII confirms that endotoxin in the blood of the animals is adsorbed by the polypropylene beads and that the endotoxin is tightly bound to the bead surfaces as demonstrated in Example V.

Obviously, many modifications and variations of the invention as hereinbefore set forth may be made without departing from the spirit and scope thereof, and, therefore, only such limitations should be imposed as are indicated in the appended claims.

I claim as my invention:

1. A process for selectively removing endotoxin derived from gram-negative bacilli from biological fluids, said process comprising:
   intimately contacting a biological fluid contaminated with gram-negative bacilli derived endotoxin with a non-ionogenic hydrophobic non-polar aliphatic synthetic plastic polymer selected from the group consisting of a substantially crystalline non-polar aliphatic hydrocarbon thermoplastic polymer, a substantially crystalline non-polar aliphatic thermoplastic fluorocarbon polymer, a cross-linked aliphatic silicone elastomeric polymer and mixtures thereof, whereby the endotoxin is adsorbed onto the surface of the polymer; and
   removing the biological fluid from contact with said polymer essentially free of said endotoxin.

2. The process of claim 1 wherein said synthetic plastic polymer is a substantially crystalline non-polar aliphatic hydrocarbon thermoplastic polymer.

3. The process of claim 2 wherein said substantially crystalline non-polar aliphatic hydrocarbon thermoplastic polymer is a poly-α-olefin polymer.

4. The process of claim 3 wherein said poly-α-olefin polymer is a material selected from the group consisting of polyethylene, polypropylene and mixtures thereof.

5. The process of claim 1 wherein said synthetic plastic polymer is a substantially crystalline non-polar aliphatic thermoplastic fluorocarbon polymer.

6. The process of claim 5 wherein said substantially crystalline non-polar aliphatic thermoplastic fluorocarbon polymer is selected from the group consisting of polytetrafluoroethylene, fluoronated ethylene-propylene polymer, modified copolymer of tetrafluoroethylene and ethylene, and mixtures thereof.

7. The process of claim 1 wherein said synthetic plastic polymer is a cross-linked silicone elastomeric polymer.

8. The process of claim 7 wherein said cross-linked elastomeric silicone polymer is a cross-linked poly(alkyl-siloxane).

9. The process of claim 1 wherein said biological fluid is intimately contacted with said polymer by passing the biological fluid through a column containing the synthetic plastic polymer in a particulated form.

10. An in vivo hemoperfusion polymer-column process for removing endotoxin derived from gram-negative bacilli from the blood of an animal, said process comprising:
    removing blood from an animal;
    perfusing said blood through a column containing particles of a non-ionogenic hydrophobic non-polar aliphatic synthetic plastic polymer selected from the group consisting of a substantially crystalline non-polar aliphatic hydrocarbon thermoplastic polymer, a crystalline aliphatic thermoplastic fluorocarbon polymer, a cross-linked silicone elastomeric polymer and mixtures thereof, whereby gram-negative bacilli derived endotoxin is adsorbed onto the surface of the synthetic plastic polymer particles; and
    reinfusing the blood passing from said column into the animal.

11. The process of claim 10 wherein said non-ionogenic hydrophobic non-polar aliphatic synthetic plastic polymer is a substantially crystalline non-polar aliphatic hydrocarbon thermoplastic polymer.

12. The process of claim 11 wherein said substantially crystalline non-polar aliphatic hydrocarbon thermoplastic polymer is a poly-α-olefin.

13. The process of claim 12 wherein said poly-α-olefin polymer is a polymer selected from the group consisting of polyethylene, polypropylene and mixtures thereof.

14. The process of claim 10 wherein said synthetic plastic polymer is a substantially crystalline aliphatic thermoplastic fluorocarbon polymer.

15. The process of claim 10 wherein said synthetic plastic polymer is a cross-linked silicone elastomeric polymer.

* * * * *